(12) United States Patent
Cosmescu (10) Patent No.: US 11,534,237 B2
(45) Date of Patent: *Dec. 27, 2022

(54) ULTRAPOLAR ELECTROSURGERY BLADE AND ULTRAPOLAR ELECTROSURGERY PENCIL

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 283 days.

This patent is subject to a terminal disclaimer.

(21) Appl. No.: 16/850,367

(22) Filed: Apr. 16, 2020

(65) Prior Publication Data

US 2020/0237431 A1 Jul. 30, 2020

Related U.S. Application Data

(63) Continuation of application No. 15/211,270, filed on Jul. 15, 2016, now Pat. No. 10,722,299.

(51) Int. Cl.
*A61B 18/12* (2006.01)
*A61B 18/14* (2006.01)
*A61B 18/00* (2006.01)

(52) U.S. Cl.
CPC ......... *A61B 18/149* (2013.01); *A61B 18/148* (2013.01); *A61B 18/1477* (2013.01); *A61B 2018/00607* (2013.01); *A61B 2018/00958* (2013.01); *A61B 2018/1467* (2013.01)

(58) Field of Classification Search
CPC ............ A61B 18/1402; A61B 18/1447; A61B 18/148; A61B 18/149; A61B 2018/000607; A61B 2018/00958; A61B 2018/1467; A61B 2018/162

See application file for complete search history.

(56) References Cited

U.S. PATENT DOCUMENTS

| | | | |
|---|---|---|---|
| 4,232,676 A | 11/1980 | Herczog | |
| 4,823,791 A | 4/1989 | D'Amelio et al. | |
| 4,850,353 A | 7/1989 | Stasz et al. | |
| 5,013,312 A | 5/1991 | Parins et al. | |
| 5,171,311 A | 12/1992 | Rydell et al. | |
| 5,908,420 A * | 6/1999 | Parins | A61B 18/1445 606/174 |
| 6,277,114 B1 | 8/2001 | Bullivant | |
| 6,432,104 B1 * | 8/2002 | Durgin | A61B 18/1477 606/49 |
| 8,177,783 B2 * | 5/2012 | Davison | A61B 18/1402 606/41 |
| 2003/0125732 A1 | 7/2003 | Goble | |

(Continued)

OTHER PUBLICATIONS

International Search Report and the Written Opinion of the International Searching Authority from related PCT Application No. PCT/US2017/031137 dated Jul. 25, 2017.

*Primary Examiner* — Daniel W Fowler
(74) *Attorney, Agent, or Firm* — Zeman-Mullen & Ford, LLP (57) ABSTRACT

An ultrapolar electrosurgery blade and an ultrapolar electrosurgery pencil. The ultrapolar electrosurgery blade has a non-conductive planar member with opposing planar sides, a cutting end, and an opposite non-cutting end, first active and return electrodes located on one opposing planar side, and second active and return electrodes located on the other opposing planar side.

18 Claims, 4 Drawing Sheets

(56) References Cited

U.S. PATENT DOCUMENTS

| | | |
|---|---|---|
| 2005/0113825 A1 | 5/2005 | Cosmescu |
| 2006/0025757 A1 | 2/2006 | Heim |
| 2008/0262489 A1 | 10/2008 | Steinke |
| 2009/0306659 A1 | 12/2009 | Buysse |
| 2014/0276795 A1 | 9/2014 | Batchelor et al. |

* cited by examiner

ULTRAPOLAR ELECTROSURGERY BLADE AND ULTRAPOLAR ELECTROSURGERY PENCIL

CROSS-REFERENCE TO RELATED APPLICATIONS

This application is a continuation of, and claims priority to, patent application having Ser. No. 15/211,270, entitled "Ultrapolar Electrosurgery Blade and Ultrapolar Electrosurgery Pencil," filed Jul. 15, 2016, which is herein incorporated by reference in its entirety.

FIELD OF INVENTION

The present invention is generally directed to an ultrapolar electrosurgery blade and an ultrapolar electrosurgery pencil which use monopolar energy in a bipolar mode for cutting and coagulation. The ultrapolar electrosurgery blade has a non-conductive planar member with first and second opposite planar sides, a cutting end, and an opposite non-cutting end, a first active electrode and a first return electrode both located on the first opposite planar side of the non-conductive planar member, and a second active electrode and a second return electrode both located on the second opposite planar side of the non-conductive planar member.

BACKGROUND OF THE INVENTION

Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monpolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

In bipolar electrosurgery, active output and patient return functions both occur at the surgery site because both the active and return electrodes are contained in the bipolar instrument. Therefore, the path of the electrical current is confined to the biological tissue located between the active and return electrodes. Although bipolar electrosurgery enables the use of lower voltages and less energy and thereby reduces or eliminates the likelihood of tissue damage and sparking associated with monopolar electrosurgery, it has limited ability to cut and coagulate large bleeding areas.

Accordingly, there is a need for an electrosurgery blade that allows for both cutting and coagulation of large areas of tissue without the tissue damage and which eliminates passing of energy through the patient. An ultrapolar electrosurgery blade having a sharp cutting edge and both active and return electrodes positioned on opposing sides of the electrosurgery blade would meet this need. The ultrapolar electrosurgery blades with a sharp cutting edge and active and return electrodes positioned on both opposing sides of the electrosurgery blade described with reference to the present invention could be used with an electrosurgery handpiece/pencil that does not have smoke evacuation capability but they are also intended to be used with an electrosurgery pencil/handpiece that is capable of smoke evacuation during the electrosurgery procedure.

SUMMARY OF THE INVENTION

The present invention is directed to an ultrapolar electrosurgery blade which includes a non-conductive planar member having first and second opposite planar sides, a cutting end, and a non-cutting end, first active and return electrodes each located on the first opposite planar side wherein at least a portion of the first opposite planar side is exposed near the cutting end of the non-conductive planar member, and second active and return electrodes each located on the second opposite planar side wherein at least a portion of the second opposite planar side is exposed near the cutting end of the non-conductive planar member. In one exemplary embodiment of the ultrapolar electrosurgery blade of the present invention, the first active electrode located on the first planar side mirrors at least a portion of the second return electrode located on the second planar side and the first return electrode located on the first planar side mirrors at least a portion of the second active electrode located on the second planar side.

The non-conductive planar member may comprise a ceramic and the first and second active electrodes and the first and second return electrodes may comprise a stainless steel, a copper, and/or a tungsten. In another exemplary embodiment of the ultrapolar electrosurgery blade of the present invention, the first and second active electrodes and the first and second return electrodes may each take the form of an elongated conductive layer that extends more than half the length of the non-conductive planar member. At least a portion of the elongated conductive layer of the first active electrode may extend to, and along a partial length of one or more of the opposing elongated edges of the first opposite planar side and at least a portion of the elongated conductive layer of the first return electrode may extend to, and along a partial length of, one or more opposing elongated edges of the first opposite planar side.

In still another exemplary embodiment of the ultrapolar electrosurgery blade of the present invention, at least a portion of the elongated conductive layer of the second return electrode on the second opposite planar side of the non-conductive planar member mirrors at least a portion of the elongated conductive layer of the first active electrode on the first opposite planar side of the non-conductive planar member and at least a portion of the elongated conductive layer of the second active electrode on the second opposite planar side of the non-conductive planar member mirrors at least a portion of the elongated conductive layer of the first return electrode on the first opposite planar side of the non-conductive planar member.

In yet another exemplary embodiment of the ultrapolar electrosurgery blade of the present invention, the ultrapolar electrosurgery blade includes a non-conductive planar member having first and second opposite planar sides with opposing elongated edges, a cutting end, and an opposite non-cutting end, a first active electrode having a hook-shaped configuration located on the first opposite planar side of the non-conductive planar member, a first return electrode having a bar-shaped configuration with at least a portion of the first return electrode positioned within the hook-shaped configuration of the first active electrode without touching the first active electrode, a second return electrode having a hook-shaped configuration located on the second opposite planar side of the non-conductive planar member, and a second active electrode having a bar-shaped configuration with at least a portion of the second active electrode positioned within the hook-shaped configuration of the second return electrode without touching the second return electrode. The hook-shaped configuration of the first active electrode and the second return electrode may be located near the cutting end of the non-conductive planar member without covering at least a portion of the first and second opposite planar sides located near the cutting end of the non-conductive planar member. At least a portion of the hook-shaped configuration of the first active electrode located on the first opposite planar side may mirror at least a portion of the hook-shaped configuration of the second return electrode located on the second opposite planar side and at least a portion of the bar-shaped configuration of the first return electrode may mirror at least a portion of the bar-shaped configuration of the second active electrode. The non-conductive planar member may comprise a ceramic and the first and second active electrodes and the first and second return electrodes may comprise a stainless steel, a copper, and/or a tungsten.

The first active electrode may take the form of a hook-shaped conductive layer where at least a portion of the hook-shaped conductive layer extends to, and along a partial length of, the opposing elongated edges of the first opposite planar side of the non-conductive planar member and the first return electrode may take the form of a bar-shaped conductive layer where at least a portion of the bar-shaped conductive layer extends to, and along a partial length of, one of the opposing elongated edges of the first opposite planar side of the non-conductive planar member. Similarly, the second return electrode may take the form of a hook-shaped conductive layer where at least a portion of the hook-shaped conductive layer extends to, and along a partial length of, the opposing elongated edges of the second opposite planar side of the non-conductive planar member and the second active electrode may take the form of a bar-shaped conductive layer where at least a portion of the bar-shaped conductive layer extends to, and along a partial length of, one of the opposing elongated edges of the second opposite planar side of the non-conductive planar member.

Further, a portion of the first and second active electrodes and a portion of the first and second return electrodes may extend to the opposite non-cutting end of the non-conductive planar member. The ultrapolar electrosurgery blade of the present invention may further comprise a first conductive insert member in communication with both the first active electrode and second active electrode located near the non-cutting end of the non-conductive planar member and a second conductive insert member in communication with both the first return electrode and the second return electrode located near the non-cutting end of the non-conductive planar member. The first and second conductive inserts may each comprise a metal contact member that is made of brass and/or copper.

The present invention is also directed to an ultrapolar electrosurgery pencil having a handpiece with a first and second end and an electrosurgery blade positioned in the first end of the handpiece where the electrosurgery blade includes a non-conductive planar member having first and second opposite planar sides, a cutting end, and an opposite non-cutting end, first active and return electrodes located on the first opposite planar side where at least a portion of the first opposite planar side is exposed near the non-conductive cutting end of the non-conductive planar member, and second active and return electrodes located on the second opposite planar side where at least a portion of the second opposite planar side is exposed near the non-conductive cutting end of the non-conductive planar member. The handpiece may further comprise a smoke evacuation channel contained therein for evacuating smoke and debris from the surgical site during activation of the electrosurgery pencil. In addition, the handpiece may further comprise at least one activation button for cutting and at least one activation button for coagulation.

BRIEF DESCRIPTION OF THE DRAWINGS

The subject invention will hereafter be described in conjunction with the appended drawing figures, wherein like numerals denote like elements.

DETAILED DESCRIPTION OF EXEMPLARY EMBODIMENTS

The exemplary embodiments of the ultrapolar electrosurgery blade and the ultrapolar electrosurgery pencil of the present invention enable a user or surgeon to perform cutting with the sharp non-conductive tip of the electrosurgery blade as well as coagulation of large areas of biological tissue with the electrosurgery blade by placing the electrosurgery blade on either of its sides where both active and return electrodes are located. The electrosurgery blade and electrosurgery pencil of the present invention may also perform cutting with the active and return electrodes of the electrosurgery blade. Exemplary embodiments of the ultrapolar electrosurgery blade and the ultrapolar electrosurgery pencil of the present invention include an electrosurgery blade that has a non-conductive planar member with opposite planar sides, a cutting end, and a non-cutting end, first active and return electrodes each located on one opposite planar side of the non-conductive planar member, and second active and return electrodes each positioned on the other opposite planar side of the non-conductive return electrode. The cutting end of the non-conductive planar member can form a sharp non-conductive cutting end for cutting biological tissue while the active and return electrodes located on each side of the non-conductive planar member can be used to perform coagulation as well as cutting of biological tissue.

Figure 1:
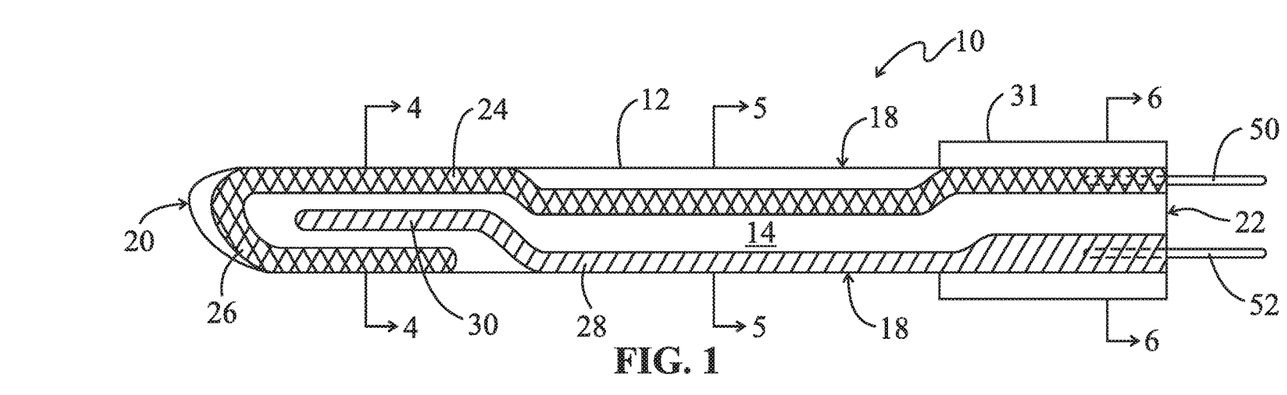
FIG. 1 is a side view of an exemplary embodiment of the ultrapolar electrosurgery blade of the present invention.
Figure 2:
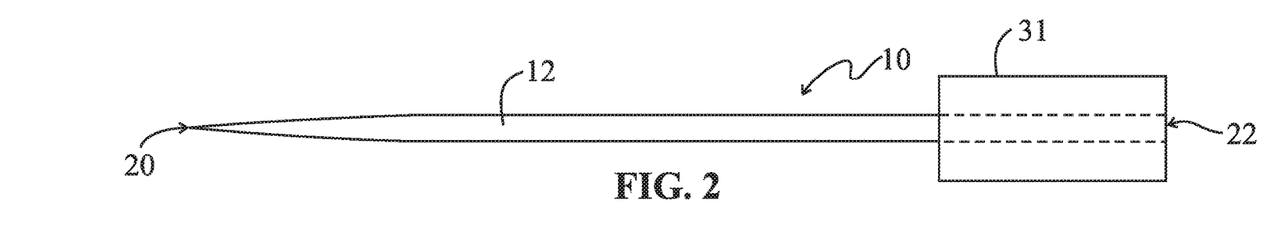
FIG. 2 is a top plan view of the exemplary embodiment of the ultrapolar electrosurgery blade of the present invention shown in FIG. 1.
Figure 3:
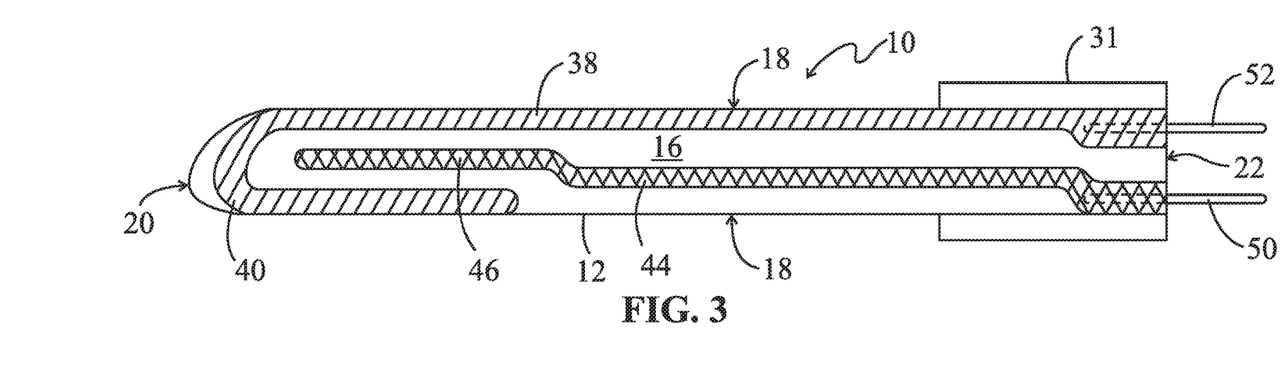
FIG. 3 is an opposite side view of the exemplary embodiment of the ultrapolar electrosurgery blade of the present invention shown in FIG. 1 with the ultrapolar electrosurgery blade in FIG. 1 shown rotated 180 degrees.

FIGS. 1 and 3 show opposing side views of an exemplary embodiment of the ultrapolar electrosurgery blade 10 of the present invention which includes a non-conductive planar member 12 having first and second opposite planar sides 14 (see FIG. 1), 16 (see FIG. 2) with opposing elongated edges 18, a cutting end 20, and an opposite non-cutting end 22, a first active electrode 24 and a first return electrode 28 each located on the first opposite planar side 14 of the non-conductive planar member 12 wherein at least a portion of the first opposite planar side 14 is exposed near the non-conductive cutting end 20 of the non-conductive planar member 12, and a second active electrode 44 and a second return electrode 38 each located on the second opposite planar side 16 of the non-conductive planar member 12 wherein at least a portion of the second opposite planar side 16 is exposed near the non-conductive cutting end 20 of the non-conductive planar member 12. First and second active electrodes 24, 44 and first and second return electrodes 28, 38 may each take the form of an elongated conductive layer that extends more than half the length of the non-conductive planar member 12.

As shown in the exemplary embodiment shown in FIGS. 1 and 3, at least a portion of the first active electrode 24 and at least a portion of the first return electrode 28 may extend to, and along a partial length of at least one of the opposing elongated edges 18 of the first opposite planar side 14 of the non-conductive planar member 12. Further, at least a portion of the second return electrode 38 may extend to, and along a partial length of, at least one of the opposing elongated edges 18 of the second opposite planar side 16 of the non-conductive planar member 12. As further shown in the exemplary embodiment of the ultrapolar electrosurgery blade shown in FIGS. 1 and 3, at least a portion of the first active electrode 24 located on the first opposite planar side 14 may mirror least a portion of the second return electrode 38 located on the second opposite planar side 16 and at least a portion of the first return electrode 28 located on the first opposite planar side 14 may mirror at least a portion of the second active electrode 44 located on the second opposite planar side 16. Moreover, the first active electrode 24 may include a hook-shaped configuration 26 and the first return electrode 28 may include a bar-shaped configuration 30 where at least a portion of the bar-shaped configuration 30 of the first return electrode 28 is positioned within the hook-shaped configuration 26 of the first active electrode 24. In addition, the second return electrode 38 may include a hook-shaped configuration 40 and the second active electrode 44 may include a bar-shaped configuration 46 where at least a portion of the bar-shaped configuration 46 of the second active electrode 44 is positioned within the hook-shaped configuration 40 of the second return electrode 38.

The non-conductive planar member 12 may comprises a ceramic which can also form a sharp cutting end 20. First and second active electrodes 24, 44 and first and second return electrodes 28, 38 may comprise at least one of stainless steel, copper, and/or tungsten. The hook-shaped configuration 26 of the first active electrode 24 and the hook-shaped configuration 40 of the second return electrode 38 may be located near cutting end 20 of non-conductive planar member 12 while still enabling at least a portion of the first and second opposite sides 14, 16 of the non-conductive planar member 12 to be exposed near the non-conductive cutting end 20. This enables precise cutting to be performed with the sharp non-conductive cutting end 20 of the ultrapolar electrosurgery blade 10.

Ultrapolar electrosurgery blade 10 may also include a support member 31 which may take the form of a variety of configurations as long as it is capable of supporting the non-conductive planar member 12 and its associated active and return electrodes so that the ultrapolar electrosurgery blade 10 may be easily connected to an instrument such as an electrosurgery pencil. Ultrapolar electrosurgery blade 10 may also include a first conductive insert member 50 that is in communication with the first active electrode 24 and the second active electrode 44 near the opposite non-cutting end 22 of the non-conductive planar member 12 and a second conductive insert member 52 that is in communication with the first return electrode 28 and the second return electrode 38 near the opposite non-cutting end 22 of the non-conductive planar member.

Figure 4:
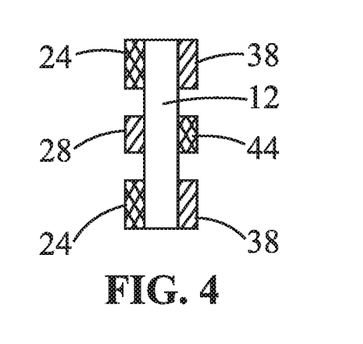
FIG. 4 is a cross-sectional view taken along line 4-4 of FIG. 1.
Figures 5, 6, 7:
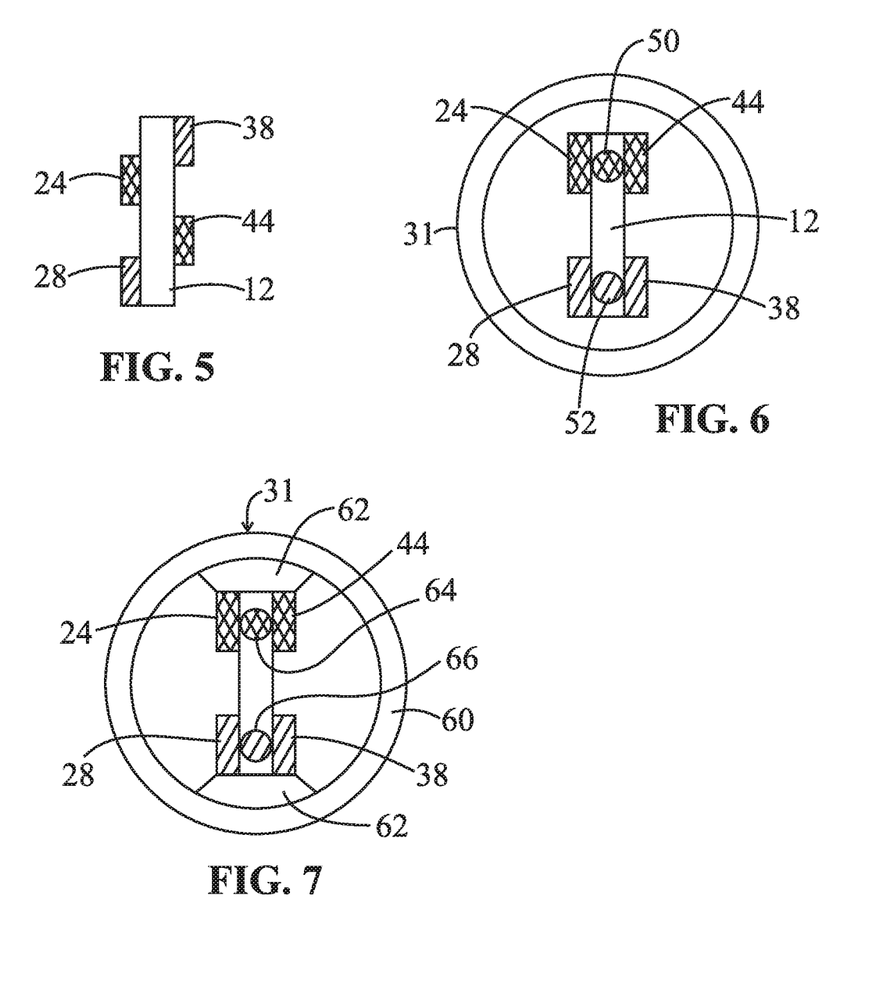
FIG. 5 is a cross-sectional view taken along line 5-5 of FIG. 1.
FIG. 6 is a cross-sectional view taken along line 6-6 of FIG. 1.
FIG. 7 is an end view of the ultrapolar electrosurgery blade of FIGS. 1 and 3 showing one exemplary embodiment of a support member for retaining the ultrapolar electrosurgery blade of the present invention so that the conductive inserts in communication with the active and return electrodes of the electrosurgery blade can be easily inserted into an electrosurgery pencil.

FIG. 2 is a top view of the ultrapolar electrosurgery blade 10 of the present invention with the non-conductive planar member 12 shown in phantom within the support member 31. FIG. 4 is a cross-sectional view taken along line 4-4 of FIG. 1 which shows non-conductive planar member 12 and first active electrode 24 and first return electrode 28 located on one side (first opposite planar side 14) of non-conductive planar member 12 and second active electrode 44 and second return electrode 38 located on the other side (second opposite planar side 16) of non-conductive planar member 12. As shown in FIG. 4, there are two portions of first active electrode 24 shown on one side of non-conductive planar member 12 and two portions of second return electrode 38 shown on the other side of non-conductive planar member 12 due to where the cross-section was taken. FIG. 5 shown another cross-section of the ultrapolar electrosurgery blade 10 of the present invention taken along line 5-5 of FIG. 1. FIG. 5 shows one portion of first active electrode 24 and one portion of first return electrode 28 on one side of non-conductive planar member 12 and one portion of second active electrode 44 and one portion of second return electrode 38 on the other side of non-conductive planar member 12. FIG. 6 is a cross-sectional view taken along line 6-6 of FIG. 1 which shows non-conductive planar member 12 along with first and second active electrodes 24, 44 and first and second return electrodes 28, 38 suspended within support member 31. FIG. 6 also shows first conductive insert member 50 of ultrapolar electrosurgery blade 10 in communication with first and second active electrodes 24, 44 and second conductive insert member 52 of ultrapolar electrosurgery blade 10 in communication with first and second return electrodes 28, 38.

An end view of the ultrapolar electrosurgery blade 10 of FIGS. 1 and 3 showing one exemplary embodiment of a support member 31 for retaining the ultrapolar electrosurgery blade 10 of the present invention so that the conductive inserts 50, 52 in communication with the active and return electrodes 24, 44, 28, 38 of the electrosurgery blade 10 can be easily inserted into an instrument such as an electrosurgery pencil. In just one exemplary embodiment, support member 31 may take the form of a hollow cylindrical member 60 having a non-conductive insert member 62 with conductive tubular members 64, 66 into which first and second conductive insert members 50, 52 can be placed. It will be understood by those skilled in the art that the support member for retaining the ultrapolar electrosurgery blade 10 of the present invention may take any number of forms or configurations.

Figure 8:
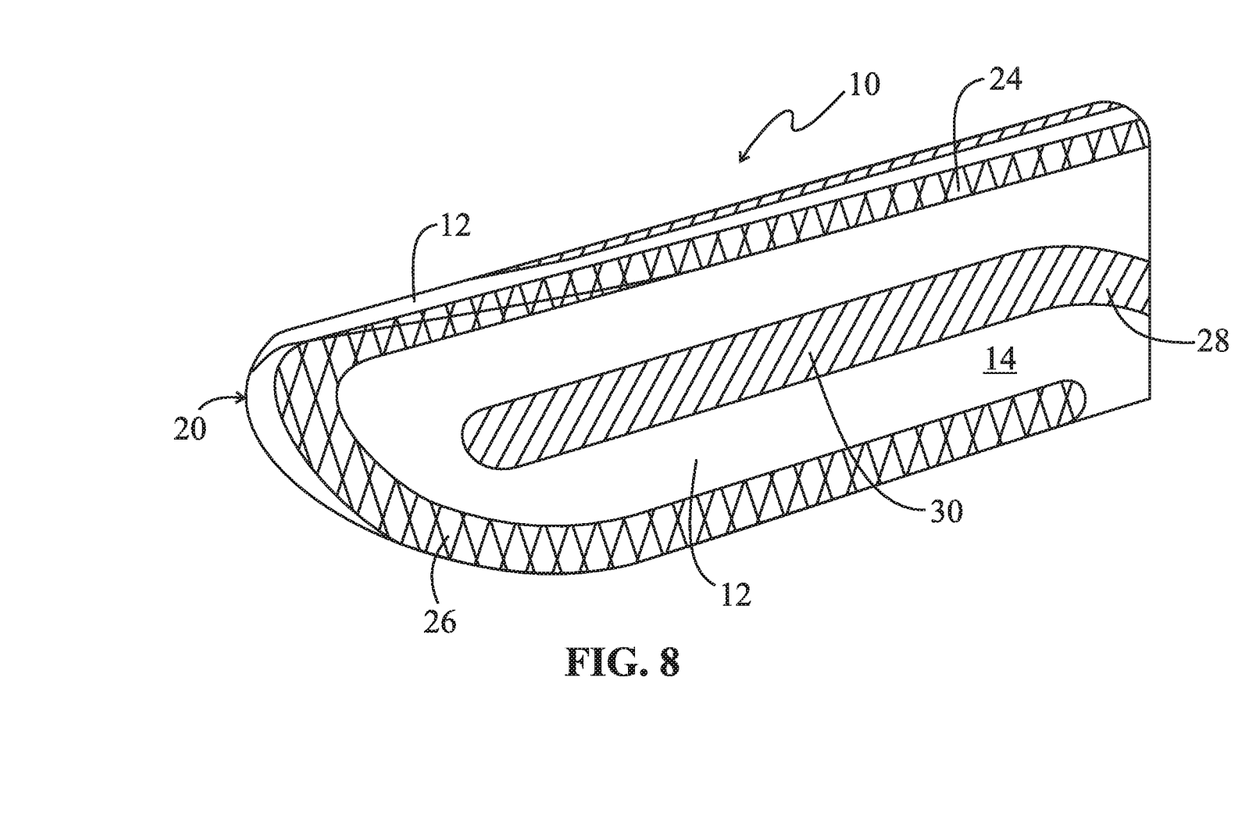
FIG. 8 is a partial perspective view of the exemplary embodiment of the ultrapolar electrosurgery blade of the present invention shown in FIG. 1.

FIG. 8 is a partial perspective view of the exemplary embodiment of the ultrapolar electrosurgery blade 10 of the present invention shown in FIG. 1. As can be seen in FIG. 8, the active and return electrodes of the blade are placed on opposite planar sides of the non-conductive planar member 12 with the top of non-conductive planar member 12 remaining non-conductive and free of electrodes.

Figure 9:
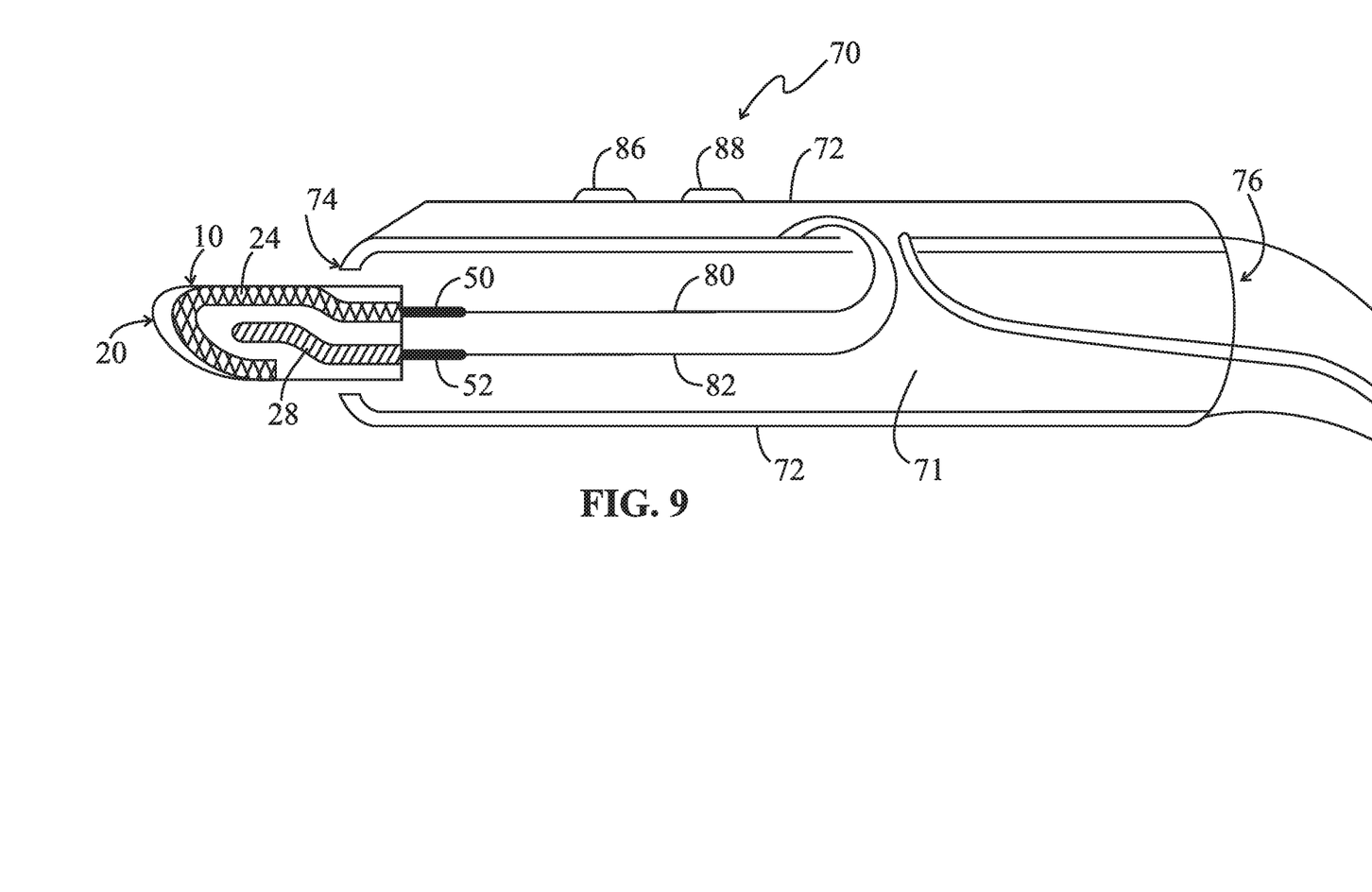
FIG. 9 is a side cross-sectional view of an exemplary embodiment of an ultrapolar electrosurgery pencil of the present invention.

A side cross-sectional view of an exemplary embodiment of an ultrapolar electrosurgery pencil 70 of the present invention is shown in FIG. 9. Ultrapolar electrosurgery pencil 70 includes a handpiece 72 having a first end 74 and a second 76, and an ultrapolar electrosurgery blade 10 positioned within the first end 74 of the handpiece. The ultrapolar electrosurgery blade 10 shown in FIG. 9 is like the blade 10 shown in FIGS. 1-3. Conductive wires 80, 82 connect the first and second conductive insert members 50, 52 to the circuit board which enables at least one activation button 86 for cutting and at least one activation button 88 for coagulation. Handpiece 72 may include a smoke evacuation channel 71 to enable evacuation of smoke and/or debris form the surgical site when performing cutting and/or coagulation.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. An ultrapolar electrosurgery blade comprising:
a non-conductive planar member having first and second opposite planar sides with opposing elongated edges, a cutting end, and an opposite non-cutting end;
a first active electrode comprising a hook-shaped configuration located on the first opposite planar side of the non-conductive planar member;
a first return electrode comprising a bar-shaped configuration wherein a bar-shaped portion of the first return electrode is positioned within the hook-shaped configuration of the first active electrode without touching the first active electrode and a bar shaped portion of the first return electrode extends to, and along a partial length of, one of the opposing elongated edges of the first opposite planar side of the non-conductive planar member;
a second return electrode comprising a hook-shaped configuration located on the second opposite planar side of the non-conductive planar member; and
a second active electrode comprising a bar-shaped configuration wherein a bar shaped portion of the second active electrode is positioned within the hook-shaped configuration of the second return electrode without touching the second return electrode.

2. The ultrapolar electrosurgery blade of claim 1 wherein the hook-shaped configuration of the first active electrode and the hook-shaped configuration of the second return electrode are located near the cutting end of the non-conductive planar member.

3. The ultrapolar electrosurgery blade of claim 1 wherein a bar-shaped portion of the second return electrode extends to, and along a length of, one of the opposing elongated edges of the second opposite planar side of the non-conductive planar member.

4. The ultrapolar electrosurgery blade of claim 1 wherein at least a portion of the hook-shaped configuration of the first active electrode located on the first opposite planar side mirrors at least a portion of the hook-shaped configuration of the second return electrode located on the second opposite planar side and at least a portion of the bar-shaped configuration of the first return electrode located on the first opposite planar side mirrors at least a portion of the bar-shaped configuration of the second active electrode located on the second opposite planar side.

5. The ultrapolar electrosurgery blade of claim 1 wherein a portion of the first and second active electrodes and a portion of the first and second return electrodes extend to the opposite non-cutting end of the non-conductive planar member.

6. The ultrapolar electrosurgery blade of claim 1 further comprising a first conductive insert member in communication with the first active electrode and second active electrode located near the opposite non-cutting end of the non-conductive planar member and a second conductive insert member in communication with the first return electrode and the second return electrode located near the opposite non-cutting end of the non-conductive planar member.

7. The ultrapolar electrosurgery blade of claim 6 wherein the first and second conductive inserts each comprise a metal contact member comprising at least one of a brass and a copper.

8. An ultrapolar electrosurgery pencil comprising:
a handpiece having a first end and a second end;
an electrosurgery blade positioned within the first end of the handpiece wherein said electrosurgery blade comprises:
a non-conductive planar member having first and second opposite planar sides with opposing elongated edges, a cutting end, and an opposite non-cutting end;
a first active electrode comprising a hook-shaped configuration located on the first opposite planar side of the non-conductive planar member;
a first return electrode comprising a bar-shaped configuration wherein a bar-shaped portion of the first return electrode is positioned within the hook-shaped configuration of the first active electrode without touching the first active electrode and a bar shaped portion of the first return electrode extends to, and along a partial length of, one of the opposing elongated edges of the first opposite planar side of the non-conductive planar member;

a second return electrode comprising a hook-shaped configuration located on the second opposite planar side of the non-conductive planar member; and a second active electrode comprising a bar-shaped configuration wherein a bar shaped portion of the second active electrode is positioned within the hook-shaped configuration of the second return electrode without touching the second return electrode.

9. The ultrapolar electrosurgery handpiece of claim 8 wherein the handpiece further comprises a smoke evacuation channel contained therein.

10. The ultrapolar electrosurgery handpiece of claim 8 wherein the handpiece comprises at least one activation button for cutting and at least one activation button for coagulation.

11. An ultrapolar electrosurgery blade comprising:
a non-conductive planar member having first and second opposite planar sides with opposing elongated edges, a cutting end, and an opposite non-cutting end;
a first active electrode comprising a hook-shaped configuration located on the first opposite planar side of the non-conductive planar member;
a first return electrode comprising a bar-shaped configuration wherein a bar-shaped portion of the first return electrode is positioned within the hook-shaped configuration of the first active electrode without touching the first active electrode and wherein another bar shaped portion of the first return electrode extends to, and along a partial length of, one of the opposing elongated edges of the first opposite planar side of the non-conductive planar member;
a second return electrode comprising a hook-shaped configuration located on the second opposite planar side of the non-conductive planar member with a bar-shaped portion that extends to, and along a length of, one of the opposing elongated edges of the second opposite planar side of the non-conductive planar member; and
a second active electrode comprising a bar-shaped configuration wherein a bar shaped portion of the second active electrode is positioned within the hook-shaped configuration of the second return electrode without touching the second return electrode.

12. The ultrapolar electrosurgery blade of claim 11 wherein the hook-shaped configuration of the first active electrode and the hook-shaped configuration of the second return electrode are located near the cutting end of the non-conductive planar member.

13. The ultrapolar electrosurgery blade of claim 11 wherein at least a portion of the hook-shaped configuration of the first active electrode located on the first opposite planar side mirrors at least a portion of the hook-shaped configuration of the second return electrode located on the second opposite planar side and at least a portion of the bar-shaped configuration of the first return electrode located on the first opposite planar side mirrors at least a portion of the bar-shaped configuration of the second active electrode located on the second opposite planar side.

14. The ultrapolar electrosurgery blade of claim 11 wherein a portion of the first and second active electrodes and a portion of the first and second return electrodes extend to the opposite non-cutting end of the non-conductive planar member.

15. The ultrapolar electrosurgery blade of claim 11 further comprising a first conductive insert member in communication with the first active electrode and second active electrode located near the opposite non-cutting end of the non-conductive planar member and a second conductive insert member in communication with the first return electrode and the second return electrode located near the opposite non-cutting end of the non-conductive planar member.

16. An ultrapolar electrosurgery pencil comprising:
a handpiece having a first end and a second end;
an electrosurgery blade positioned within the first end of the handpiece wherein said electrosurgery blade comprises:
a non-conductive planar member having first and second opposite planar sides with opposing elongated edges, a cutting end, and an opposite non-cutting end;
a first active electrode comprising a hook-shaped configuration located on the first opposite planar side of the non-conductive planar member;
a first return electrode comprising a bar-shaped configuration wherein a bar-shaped portion of the first return electrode is positioned within the hook-shaped configuration of the first active electrode without touching the first active electrode and wherein another bar-shaped portion of the first return electrode extends to, and along a partial length of, one of the opposing elongated edges of the first opposite planar side of the non-conductive planar member;
a second return electrode comprising a hook-shaped configuration located on the second opposite planar side of the non-conductive planar member with a bar-shaped portion that extends to, and along a length of, one of the opposing elongated edges of the second opposite planar side of the non-conductive planar member; and
a second active electrode comprising a bar-shaped configuration wherein a bar shaped portion of the second active electrode is positioned within the hook-shaped configuration of the second return electrode without touching the second return electrode.

17. The ultrapolar electrosurgery handpiece of claim 16 wherein the handpiece further comprises a smoke evacuation channel contained therein.

18. The ultrapolar electrosurgery handpiece of claim 16 wherein the handpiece comprises at least one activation button for cutting and at least one activation button for coagulation.

* * * * *